United States Patent
Lattner et al.

(10) Patent No.: US 7,485,767 B2
(45) Date of Patent: Feb. 3, 2009

(54) PRODUCTION OF SYNTHESIS GAS BLENDS FOR CONVERSION TO METHANOL OR FISCHER-TROPSCH LIQUIDS

(75) Inventors: James R. Lattner, Seabrook, TX (US); Christopher D. W. Jenkins, South Caulfield (AU)

(73) Assignee: ExxonMobil Chemical Patents Inc., Houston, TX (US)

( * ) Notice: Subject to any disclaimer, the term of this patent is extended or adjusted under 35 U.S.C. 154(b) by 651 days.

(21) Appl. No.: 11/211,982

(22) Filed: Aug. 25, 2005

(65) Prior Publication Data
US 2007/0004809 A1 Jan. 4, 2007

Related U.S. Application Data

(60) Provisional application No. 60/695,728, filed on Jun. 29, 2005.

(51) Int. Cl.
C01B 3/24 (2006.01)
C01B 3/26 (2006.01)
C07C 27/06 (2006.01)
C07C 5/00 (2006.01)

(52) U.S. Cl. .................. 585/639; 252/373; 518/703
(58) Field of Classification Search ............... 252/373; 518/703; 585/639
See application file for complete search history.

(56) References Cited

U.S. PATENT DOCUMENTS

| 5,252,609 | A | 10/1993 | Pinto |
| 5,496,859 | A | 3/1996 | Fong et al. |
| 6,224,789 | B1 | 5/2001 | Dybkjaer ........... 252/373 |
| 6,402,988 | B1 | 6/2002 | Gottzmann et al. ....... 252/373 |
| 6,444,712 | B1 | 9/2002 | Janda |
| 6,773,691 | B2* | 8/2004 | Ramani et al. ........... 423/651 |
| 2004/0182002 | A1 | 9/2004 | Malhotra et al. |
| 2004/0241086 | A1 | 12/2004 | Van Dongen et al. ....... 423/651 |

FOREIGN PATENT DOCUMENTS

| EP | 1 403 216 | 3/2004 |
| WO | WO 93/15999 | 8/1993 |
| WO | WO 2004/092060 | 10/2004 |

(Continued)

OTHER PUBLICATIONS

Asaberg-Petersen et al, "Technologies for Large-Scale Gas Conversion", Applied Catalysis, A; General (2001), 221 (1-2), pp. 379-387.

(Continued)

*Primary Examiner*—Wayne Langel (57) ABSTRACT

The present invention provides a process for producing synthesis gas blends which are especially suitable for conversion either into oxygenates such as methanol or into Fischer-Tropsch liquids. Such a process involves reforming of two separate gaseous hydrocarbon feedstreams (formed, for example, by dividing a natural gas feedstock) in a steam-reforming unit and an oxygen-blown reforming unit, respectively. The syngas effluent from each reforming unit is then combined, after appropriate pressure adjustments, to realize a synthesis gas blend containing selected amounts and ratios of $H_2$, CO and $CO_2$. In further invention embodiments, processes are provided for converting the resulting syngas blends into oxygenates or Fischer-Tropsch hydrocarbons. Further conversion of the oxygenates so produced into light olefins also constitutes part of this invention.

19 Claims, 3 Drawing Sheets

FOREIGN PATENT DOCUMENTS

| | | |
|---|---|---|
| WO | WO 2004/092061 | 10/2004 |
| WO | WO 2004/092062 | 10/2004 |
| WO | WO 2004/092063 | 10/2004 |
| WO | WO 2004/096952 | 11/2004 |

OTHER PUBLICATIONS

Dybkj. Aeligat, R., IB, "Tubular Reforming and Autothermal Reforming of Natural Gas—An Overview of Available Processes", Fuel Processing Technology (1995), 42 (2+3), pp. 85-107.

* cited by examiner

PRODUCTION OF SYNTHESIS GAS BLENDS FOR CONVERSION TO METHANOL OR FISCHER-TROPSCH LIQUIDS

CROSS REFERENCE TO RELATED APPLICATIONS

This application claims the benefit of Provisional Application No. 60/695,728 filed Jun. 29, 2005, the disclosure of which is fully incorporated herein by reference.

FIELD OF THE INVENTION

The present invention relates to processes for producing blends of synthesis gas which are suitable for catalytic conversion to either oxygenates, such as methanol and/or dimethyl ether, or to Fischer-Tropsch liquids.

BACKGROUND OF THE INVENTION

Methanol is one of the major chemical raw materials, ranking third in volume behind ammonia and ethylene. Worldwide demand for methanol as a chemical raw material continues to rise especially in view of its increasingly important role (along with dimethyl ether) as a source of olefins such as ethylene and propylene and as an alternative energy source, for example, as a motor fuel additive or in the conversion of methanol to gasoline.

Another commercially important source of hydrocarbons for use as fuels, lubricants and other petrochemical feedstocks are liquids derived via the Fischer-Tropsch procedure. The Fischer-Tropsch process was developed in the 1920's as a way of synthetically producing higher hydrocarbons from lower hydrocarbon-containing feedstocks. Initially the process was centered on producing gasoline range hydrocarbons as automotive fuels. More recently, the Fischer-Tropsch process has been viewed as a viable method for preparing even heavier hydrocarbons such as diesel fuels, and more preferably waxy molecules for conversion to clean, efficient lubricants.

Both methanol (as well as dimethyl ether) and Fischer-Tropsch liquids can be produced via the catalytic conversion of a gaseous feedstock comprising hydrogen, carbon monoxide and carbon dioxide. Such a gaseous mixture is commonly referred to as synthesis gas or "syngas".

Methanol is typically produced from the catalytic reaction of syngas in a methanol synthesis reactor in the presence of a heterogeneous catalyst. For example in one synthesis process, methanol is produced using a copper/zinc catalyst in a water-cooled tubular methanol reactor. In methanol production, syngas undergoes three reactions, only two of which are independent. These reactions are:

$$2H_2 + CO \leftrightarrow CH_3OH \quad (1)$$

$$3H_2 + CO_2 \leftrightarrow CH_3OH + H_2O \quad (2)$$

$$H_2O + CO \leftrightarrow H_2 + CO_2 \quad (3)$$

As can be seen from Reactions #2 and #3, $CO_2$ can participate in methanol synthesis. Nevertheless, it is desirable to minimize the amount of $CO_2$ in the syngas for several reasons. In the first place, a low $CO_2$ content in the syngas results in a more reactive mixture for methanol synthesis provided the $CO_2$ content is at least about 2%. Furthermore, less $CO_2$ results in lower consumption of hydrogen and lower production of water. Lower water production is useful in applications where some relative small amounts of water can be present in the methanol product such as, for example, in connection with a methanol to olefins (MTO) process. Production of methanol with low water content thus eliminates the need to distill water from the syngas product methanol.

The syngas stoichiometry for methanol synthesis from syngas is generally described by the following relationship known as the "Stoichiometric Number" or $S_N$.

$$S_N = (H_2 - CO_2)/(CO + CO_2)$$

The value of $S_N$ theoretically required for methanol synthesis is 2.0. However, for commercial production of methanol from syngas, it is desirable that the value for $S_N$ range from about 2.05 to 2.10. Dimethyl ether (DME) may also be produced from syngas using chemistry similar to that used for methanol synthesis.

Syngas may also be used as the starting feedstock for production of Fischer-Tropsch liquids. The Fischer-Tropsch process is a well-known process, and the reaction conditions for it have been described in the literature. For example, temperatures may range from about 175° C. to 400° C., preferably from about 180° C. to 250° C. Pressures from about 1 to 100 bar, more preferably from about 15 to 40 bar are used. The catalysts employed in the Fischer-Tropsch process are iron and cobalt. Promoters like rhenium, zirconium, manganese and the like are commonly used to improve various aspects of catalytic performance. These catalysts and promoters are typically supported on a particulate material such as alumina or titania.

Starting with syngas, the Fischer-Tropsch synthesis proceeds according to the following reaction:

$$2H_2 + CO \leftrightarrow (1/n)(C_nH_{2n}) + H_2O$$

As can be seen from this reaction, $CO_2$ does not participate in the synthesis of Fischer-Tropsch liquids and can generally be viewed as an inert ingredient in the F-T synthesis procedure. The $H_2/CO$ ratio desired for synthesis of Fischer-Tropsch liquids is about 2.0.

Synthesis gas useful for either methanol/dimethyl ether synthesis or production of Fischer-Tropsch liquids can be obtained from a source of lower hydrocarbons, such as natural gas, via a procedure known as reforming. Various commercial reforming technologies are known in the art. All involve reaction of hydrocarbons such as methane with steam, oxygen or both Steam reforming (SR) involves the reaction of a hydrocarbon feedstock, e.g., natural gas, with steam over a suitable reforming catalyst. In general, this reaction proceeds according to the following general reaction scheme:

$$C_nH_m + nH_2O \leftrightarrow nCO + [n + m/2]H_2$$

with the water gas shift reaction (Reaction #3 above) also taking place to produce $CO_2$. For methane, this principal reaction becomes:

$$CH_4 + H_2O \leftrightarrow CO + 3H_2.$$

All of the heat needed to drive this endothermic reforming reaction is supplied externally to the catalyst bed, and no oxygen is used in the feedstock or introduced into the process. Commercial SR technologies utilize a nickel catalyst and a relatively large ratio of steam to carbon in order to prevent coking of the catalyst. The steam reforming operation generally produces syngas with a Stoichiometric Ratio $S_N$ which is above that best suited for methanol synthesis and also has excessive hydrogen beyond that which is needed for either methanol or Fischer-Tropsch synthesis. Furthermore, the $CO_2$ content in the resulting syngas can be excessive for production of either methanol for which low water content may be desired or for F-T synthesis.

Autothermal reforming (ATR) involves the addition of air or oxygen with relatively smaller proportions of steam to a hydrocarbon feedstock. Reaction of hydrocarbon with oxygen proceeds according to the following general reaction schemes:

$$C_nH_m + (n/2)O_2 \leftrightarrow nCO + (m/2)H_2 \text{ and}$$

$$C_nH_m + (n+m/4)O_2 \leftrightarrow nCO_2 + m/2 H_2O$$

When methane is the hydrocarbon undergoing oxidative reforming, these reactions become:

$$CH_4 + \tfrac{1}{2}O_2 \leftrightarrow CO + 2H_2 \text{ and}$$

$$CH_4 + 2O_2 \leftrightarrow CO_2 + 2H_2O$$

Autothermal reforming employs both steam reforming and oxidative reforming of the hydrocarbon feed. The exothermic oxidation of the feedstock hydrocarbons generates sufficient heat to drive the endothermic steam reforming reaction over the catalyst bed. The ATR procedure is thus run at relatively high temperatures and pressures with a relatively low steam to carbon ratio. The syngas resulting from autothermal reforming generally has a slight surplus of hydrogen for F-T synthesis but insufficient hydrogen and hence a Stoichiometric Ratio $S_N$ which is not high enough for methanol synthesis. The $CO_2$ content of the syngas from ATR processes, however, is fairly low, as is desirable for both methanol and F-T synthesis.

It is also known to run a combination of separate steam reforming and autothermal reforming operations for syngas production in order to provide syngas with a more suitable Stoichiometric Ratio $S_N$ for methanol production. In such a combined reforming (CR) procedure, steam is mixed with the hydrocarbon feed which is partially converted to syngas in a steam reformer with externally supplied heat. Autothermal reforming is then used to convert the rest of the hydrocarbon feedstock, either in series and/or in parallel with the SR operation. Heat from the ATR stage effluent can be used to supply the external heat needed for the SR stage. The Stoichiometric Ratio $S_N$ for the resulting syngas from CR can be made ideal for methanol synthesis, but the syngas has an excessive amount of hydrogen for Fischer-Tropsch synthesis. The relatively high steam to carbon ratio used for the SR portion of the combined reforming operation also results in a relatively high $CO_2$ content in the syngas produced due to the water gas shift reaction. Such $CO_2$ content is higher than is desirable for low-water methanol synthesis wherein minimization of water production is needed.

Another known reforming process involves primarily partial oxidation of a hydrocarbon feed with an oxygen-containing gas. Although catalytic partial oxidation reforming procedures are known, for purposes of this invention, partial oxidation reforming takes place in the absence of a catalyst. Due to the absence of a catalyst, partial oxidation (POX) reforming can operate at very high temperatures with little or no steam addition to the feedstock. Higher pressures than are used in ATR operations can be employed in POX reforming. However, the syngas composition resulting from POX reforming is generally deficient in hydrogen for either methanol or F-T synthesis, resulting in $S_N$ and $H_2$:CO numbers below 2. On the other hand, the $CO_2$ content of the resulting syngas is generally very low which is ideal for F-T synthesis but below the optimum value for methanol synthesis.

The three reforming operations hereinbefore described which employ an oxygen-containing gas to generate heat as a consequence of the reforming reaction are known as oxygen-blown reforming (OBR) processes. These OBR processes generally produce syngas at a higher temperature and pressure than the syngas produced by SR reforming processes.

It is known in the prior art to utilize various combinations of reforming operation types and procedures in the preparation of syngas mixtures which can be converted, for instance, into oxygenates. For example, Texaco's U.S. Pat. No. 5,496,859 discloses a method for the production of a "stoichiometric ratioed syngas". The method comprises partially oxidizing a gaseous feedstock containing substantial amounts of methane in a gasifier to produce a hot synthesis gas stream that is passed in indirect heat exchange through a steam reforming catalytic reactor. A portion of the steam reforming reaction products are mixed with the cooled gasifier synthesis gas stream exiting the steam reforming catalytic reactor to form a stoichiometric ratioed synthesis gas. The stoichiometric ratioed synthesis gas stream can then be passed into a methanol synthesis unit at substantially the specifications for optimal methanol production with little or no external compression. The stoichiometric ratio, $S_N$, in the syngas produced is said to range from 1.9 to 2.1. Syngas having an $S_N$ of 1.9 and an $H_2$/CO ratio of 2.52 are exemplified in the '859 patent. The exemplified syngas has a excessively high water content of 22%, or on a water-free basis a relatively high $CO_2$ content of 5.3%.

Haldor Topsoe's U.S. Pat. No. 6,224,789 and related publication [Aasberg-Petersen et al; *Applied Catalysis, A: General* (2001), 221 (1-2), pp 379-387] both disclose an arrangement similar to that of the Texaco '859 patent wherein effluent gas from an ATR unit circulates around and supplies heat to the HTCR (a heat exchanger version of an SR reactor), but does not undergo chemical reaction there. The exemplified Haldor Topsoe process provides a syngas with an $S_N$ stoichiometric ratio of 3.66 and an $H_2$/CO ratio of 3.25.

Shell's U.S. Published Application No. 2004/241,086 discloses a process for the preparation of syngas from a gaseous hydrocarbon feedstock by (a) partial oxidation of a part of the feedstock and (b) steam reforming of another part of the feedstock. The mixture obtained in step (b) may be directly combined with the product gas as obtained in step (a). No description of feedstock or syngas composition characterized by component concentration is given.

ICI's U.S. Pat. No. 5,252,609 discloses a syngas production process involving the SR and OBR treatment of two separate hydrocarbon feedstock streams. Such a process comprises (a) steam reforming a first stream of desulfurized hydrocarbon feedstock, optionally followed by secondary reforming using an oxygen-containing gas and then cooling, (b) steam reforming a second stream of the feedstock, preferably adding a hydrogen-containing gas, and then subjecting the product to partial oxidation with an oxygen-containing gas and then cooling, and (c) mixing the two cooled product streams.

Shell's WO 04/092062 and WO 04/092063 both disclose other syngas production processes involving a combination of different types of reforming operations. Such processes comprise (a) partial oxidation of a carbonaceous feedstock thereby obtaining a first gaseous mixture of hydrogen and carbon monoxide, (b) steam reforming a carbonaceous feedstock, wherein the steam to carbon molar ratio is below 1, to obtain as a steam reforming product, (c) feeding the steam reforming product to the upper end of the partial oxidation reactor to obtain a mixture of the effluent of step (a) and the steam reformer product, and (d) providing the required heat for the steam reforming reaction in step (b) by convective heat exchange between the mixture obtained in step (c) and the steam reformer reactor tubes, thereby obtaining a hydrogen and carbon monoxide containing gas having a reduced temperature.

Praxair/Standard Oil's U.S. Pat. No. 6,402,988 discloses the following: "An exothermic reaction and an endothermic reaction are thermally combined in a reactor having at least one oxygen selective ion transport membrane that provides the exothermic reaction with oxygen from an oxygen-containing gas such as air. The thermal requirements of the endothermic reaction are satisfied by the exothermic reaction. Dependent on the reactor design employed, the exothermic and endothermic reactions may be gaseously combined". The exothermic reaction is partial oxidation; the endothermic reaction is steam reforming.

Davy McKee's WO 93/15999 shows an arrangement, with steam reforming (SR) and partial oxidation (POX) units in parallel. The effluents are combined and in this arrangement are sent to a secondary reforming zone for further reduction in product methane content.

Notwithstanding these various reforming arrangements of the prior art, it would still be desirable to identify additional syngas preparation techniques which involve combinations of the various types of natural gas reforming operations in order to realize syngas blends suitable for both oxygenate preparation and Fischer-Tropsch synthesis. In particular, it would be desirable to operate a steam reformer in a way which takes advantage of its strengths and to also operate an oxygen-blown reforming unit under conditions which take advantage of its strengths. It would then be advantageous to combine the syngas effluent from such reforming operations in a way and under conditions which result in a syngas product blend having stoichiometry of components that is optimized for subsequent production of either methanol/dimethyl ether oxygenates or Fischer-Tropsch liquids.

SUMMARY OF THE INVENTION

The present invention provides a process for the production of synthesis gas blends which are suitable for conversion either to oxygenates comprising, for example, methanol and/or dimethyl ether or to Fischer-Tropsch liquids. Such a process comprises:

(a) passing a first gaseous hydrocarbon feedstream along with steam to a steam reforming unit to thereby provide as effluent from the steam reforming unit a first syngas effluent stream containing $H_2$ and carbon oxides;

(b) passing a second gaseous hydrocarbon feedstream along with oxygen and optionally steam to an oxygen-blown reforming unit to thereby provide as effluent from the oxygen-blown reforming unit a second syngas effluent stream also containing $H_2$ and carbon oxides;

(c) compressing the first syngas effluent stream to a pressure substantially equal to that of the second syngas effluent stream; and thereafter (d) combining the first and second syngas effluent streams to provide a unique syngas blend effluent.

Both the first and second gaseous hydrocarbon feedstreams fed to the steam reforming unit and the oxygen-blown reforming unit, respectively, preferably contain at least about 50 mol % of methane. The steam reforming unit is operated at a pressure of less than 30 bar, with the feedstream fed to it having a steam to carbon molar ratio greater than about 1.5. The oxygen-blown reforming unit is operated at a pressure of greater than 35 bar with the feedstream fed to it having an $O_2$:C molar ratio of from about 0.4 to 0.7 and a steam to carbon molar ratio of less than about 1.5.

The first and second syngas effluent streams from the respective reforming units are combined in a ratio suitable to provide a combined syngas blend having i) a Stoichiometric Ratio $S_N$ ranging from about 2.0 to 2.2; ii) an $H_2$/CO molar ratio greater than about 1.9; and iii) a $CO_2$ content of less than about 5.5 mol %. A combined effluent stream having these parameters is useful for the catalytic conversion of such a combined stream to either oxygenates such as methanol and/or dimethyl ether or to Fischer-Tropsch liquids.

BRIEF DESCRIPTION OF THE DRAWINGS

This invention will be better understood by reference to the detailed description of the invention when taken together with the accompanying drawings.

DETAILED DESCRIPTION OF THE INVENTION

The syngas blends of the present invention are formed by carrying out two separate reforming operations which start with gaseous hydrocarbon feedstreams. Such gaseous hydrocarbon feedstreams will generally primarily contain $C_1$ to $C_5$ hydrocarbons, along with smaller amounts of other materials, and can be obtained from a variety of carbon sources. Examples of such sources include biomass, natural gas, $C_1$-$C_5$ hydrocarbons, naphtha, heavy petroleum oils, or coke (i.e., coal). Preferably, the gaseous hydrocarbon feed stream comprises methane in an amount of at least about 50% by volume, more preferably at least about 70% by volume, most preferably at least about 80% by volume. Natural gas is the preferred source for the gaseous hydrocarbon feedstreams used in this invention.

Preferably the composition of the two hydrocarbon feedstreams fed to the two separate types of reforming operations will be substantially the same, or at least have substantially the same methane content. A convenient way of realizing this substantial identity of feedstream compositions is, of course, to divide a single hydrocarbon feedstream into the two separate feedstreams needed for each of the two reforming units.

Prior to being divided, the total amount of hydrocarbon feedstock fed to the process herein can vary widely depending upon equipment size and commercial needs and considerations. Preferably, when a single natural gas feedstock is divided, i.e., split, to form the two distinct gaseous hydrocarbon feedstreams used in the present process, that single natural gas feedstock can be fed to the process herein at rates ranging from about 750 to 45,000 kgmol/hr.

Preferably from about 20% to 40% of the total hydrocarbon feedstock used in the process will be sent to the steam reforming unit and from about 60% to 80% of the total hydrocarbon feedstock used in the process will be sent to the oxygen-blown reformer. In terms of the methane content of the two hydrocarbon feedsteams, preferably the ratio of moles per hour of methane fed to the steam reforming unit to moles per hour of methane fed to the oxygen-blown reforming unit will range from about 1:1 to 1:4.

The hydrocarbon feedstreams that are used in the conversion of hydrocarbon to syngas can optionally be treated to remove impurities that can cause problems in further processing of the hydrocarbon feedstreams. These impurities can poison many conventional propylene and ethylene forming catalysts. A majority of the impurities that may be present can be removed in any conventional manner. The hydrocarbon feedstreams are preferably purified to remove sulfur compounds, nitrogen compounds, particulate matter, other condensables, and/or other potential catalyst poisons prior to being converted into syngas.

The steam reforming unit employed in the process of the present invention can comprise any conventional reforming apparatus wherein the gaseous hydrocarbon feedstream can be contacted and reacted with steam in order to produce syngas containing $H_2$, CO and $CO_2$. The hydrocarbon/steam reaction is generally conducted in the presence of a catalyst and proceeds according to the chemical reactions set forth hereinbefore.

Any conventional reforming type catalyst can be used in the steam reforming unit. The catalyst used in the step of catalytic steam reforming generally comprises at least one active metal or metal oxide of Group 6 or Group 8-10 of the Periodic Table of the Elements. The Periodic Table of the Elements referred to herein is that from CRC Handbook of Chemistry and Physics, 82nd Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. Preferably, the catalyst includes from about 5 wt % to about 25 wt % of at least one Group 6 or Group 8-10 metal, based on total weight of the catalyst.

The steam reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1 weight percent metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w metal, calculated on the whole catalytic unit.

In one embodiment, the steam reforming unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the steam reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The steam reforming reaction is generally carried out such that the exit temperature of effluent from the steam reformer ranges from about 500° C. to about 1,000° C., preferably from about 750° C. to about 950° C., and more preferably from about 800° C. to about 900° C.

Gas hourly space velocity in the steam reformer should be sufficient for providing the desired CO to $CO_2$ balance in the syngas. Preferably, the gas hourly space velocity (based on wet feed) is from about 3,000 $hr^{-1}$ to 10,000 $hr^{-1}$, more preferably from about 4,000 $hr^{-1}$ to 9,000 $hr^{-1}$, and most preferably from about 5,000 $hr^{-1}$ to 8,000 $hr^{-1}$.

The use of a tubular reformer is preferred for the steam reforming operation. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, Encyclopedia of Chemical Technology, 3rd Ed., 1990, vol. 12, p. 951; and Ullmann's Encyclopedia of Industrial Chemistry, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to carbon in the feed to the steam reforming unit will generally be greater than about 1.5:1, preferably from about 1.8:1 to 4:1.

Typically, the first syngas effluent stream from the steam reforming unit comprises hydrogen and carbon oxides. The hydrogen to carbon oxide ratio of the syngas produced will vary depending on the overall conditions of the steam reformer. Preferably, the molar ratio of hydrogen to carbon oxides in the first syngas effluent stream will range from about 1:1 to about 5:1. More preferably the molar ratio of hydrogen to carbon oxides will range from about 2:1 to about 4:1. Even more preferably the molar ratio of hydrogen to carbon oxides will range from about 2:1 to about 3.5:1. Most preferably the molar ratio of hydrogen to carbon oxides will range from about 2:1 to about 3.2:1.

Steam reforming is generally carried out at superatmospheric pressure but for this invention at pressures no greater no greater than about 30 bar (3000 kPa). Steam reforming pressures of from about 10 bar (1000 kPa) to 28 bar (2800 kPa) are preferred. More preferably, steam reforming is carried out at a pressure of from about 22 bar (2200 kPa) to 27 bar (2700 kPa). As discussed in greater detail hereinafter, the first syngas effluent stream from the steam reforming unit must be compressed prior to its combination with the second syngas effluent stream from the oxygen-blown reforming unit.

The second gaseous hydrocarbon feedstream is also subjected to a reforming step. But this reforming step of the second gaseous hydrocarbon feedstream is carried out in an oxygen-blown reforming unit. The oxygen-blown reforming step involves the reaction of the second gaseous hydrocarbon feedstream with oxygen to produce $H_2$, CO and $CO_2$ in accordance with the exothermic chemical reactions set forth hereinbefore. Such an oxygen-blown reforming step may be carried out with or without steam added to the reforming unit feed. Oxygen-blown reforming may also be carried out with or without a catalyst.

Reforming in the oxygen-blown reforming unit is carried out at pressures greater than about 35 bar (3500 kPa) using an $O_2$:C molar ratio of from about 0.4:1 to 0.7:1. A steam to carbon molar ratio of less than 1.5:1 is generally utilized.

When a catalyst is used and when steam is co-fed to the oxygen-blown reforming unit, the procedure is generally known as "autothermal" reforming. When no catalyst is employed, and when no steam is co-fed to the reformer along with the second hydrocarbon feedstream (other than small amounts used for cooling purposes), the operation, for purposes of this invention, is known by the more generic term as "partial oxidation" reforming.

Autothermal reforming involves passing the second gaseous hydrocarbon feedstream and oxygen, preferably in the form of air, along with steam, over reduced or unreduced composite catalyst. Autothermal reforming is both exothermic and endothermic as a result of adding both oxygen and water (steam) to the catalytic reforming unit.

When the oxygen-blown reforming step is autothermal reforming, a suitable catalyst is generally used. The catalyst can comprise at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected from the group consisting of Ru, Rh, and Ir.

In one embodiment, the autothermal reforming catalyst can further comprise at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the autothermal reforming catalyst is at least one rare earth element selected from the group consisting of La, Ce, Pr, Nd, Pm, Sm, Eu, Gd, Tb, Dy, Ho, Er, Tm, Yb and Lu.

Preferably the autothermal reforming catalyst will comprise at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

For autothermal reforming, the catalyst is generally retained in the form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

For autothermal reforming, the $O_2$:C molar ratio in the feed will generally range from about 0.5:1 to 0.65:1, more preferably from about 0.51:1 to 0.55:1. Steam to carbon molar ratios for autothermal reforming will generally range from about 0.4:1 to 1:1, more preferably from about 0.5:1 to 0.7:1.

The autothermal reforming step is operable over a wide range of pressures. For applications on a commercial scale, elevated pressures, i.e., pressures significantly above atmospheric pressure, are preferred. In one embodiment, the autothermal reforming process is operated at pressures of greater than 35 bar (3500 kPa) atmospheric up to about 150 bar (15,000 kPa). Preferably, the autothermal reforming process is operated at a pressure in the range of from about 37 bar (3700 kPa) to about 45 bar (4500 kPa).

The autothermal reforming (ATR) step is also operable over a wide range of temperatures. In ATR, the oxygen and hydrocarbon gas mix and burn before contacting the catalyst. The feed mixture is preferably preheated prior to being fed to the ATR unit. In one embodiment, the feed mixture is fed to the ATR unit at a temperature of from about 400° C. to 700° C., more preferably form about 500° C. to 675° C., most preferably from about 550° C. to 650° C. Generally the exit temperature of gas from the ATR unit is in the range of from about 900° C. to about 1150° C., more preferably from about 1000° C. to about 1100° C.

The feed is provided during the operation of the authothermal reforming step at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

Non-catalytic partial oxidation of hydrocarbons to $H_2$, CO and $CO_2$ may also be used as the requisite oxygen-blown reforming step in the process of the present invention. The non-catalytic partial oxidation process is carried out by injecting preheated hydrocarbon, and oxygen through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1100° C. to about 1500° C., and at a pressure ranging from about 50 bar (5000 kPa) to 100 bar (10000 kPa). Throughput rates of from 500 kgmol/hr to 40,000 kgmol/hr of hydrocarbon can be employed in a partial oxidation reforming operation. Generally no steam is added to the reforming unit when non-catalytic partial oxidation reforming is carried out except for small amounts necessary to cool exposed metal parts of the high temperature burner.

In accordance with the present invention, the syngas effluent from the steam reforming unit is combined with the syngas effluent from the oxygen-blown reforming unit to provide a syngas blend effluent which is especially suitable for further processing into desired materials. Given the differences in operating conditions between the steam reforming unit and the oxygen-blown reforming unit, it will generally be necessary to pressurize the syngas effluent stream from the steam reforming unit before it is combined with the syngas effluent stream from the oxygen-blown reformer. Accordingly, the syngas effluent stream from the steam reforming unit is compressed to a pressure which is substantially equal to that of the syngas effluent stream from the oxygen-blown reforming unit. Frequently, this pressure will be that at which the combined syngas effluent blend is rendered suitable for further processing.

For methanol synthesis, syngas streams are generally compressed to a pressure of from about 35 bar to 100 bar (3500 kPa to 10000 kPa), more preferably from about 40 bar to 80 bar (4000 kPa to 8000 kPa). For F-T synthesis, syngas streams are generally compressed to a pressure of from about 15 bar to 40 bar (1500 kPa to 4000 kPa) so the combined syngas effluent blend from the reforming operations herein is also suitable as direct feed for F-T processing.

Once combined, the effluent streams from the respective reforming units should contain $H_2$, CO and $CO_2$ in amounts and ratios which render the resulting syngas effluent blend especially suitable for subsequent processing into either oxygenates comprising methanol/dimethyl ether or into Fischer-Tropsch liquids. To bring about this result for the synthesis of methanol/dimethyl ether, this means that the Stoichiometric Ratio $S_N$, which as noted hereinbefore is the molar ratio of $(H_2—CO_2)$ to $(CO+CO_2)$, should range from about 2.0 to 2.2. More preferably this Stoichiometric Ratio $S_N$ ranges from about 2.05 to 2.1, most preferably from about 2.08 to 2.09.

The syngas blend formed from the combined effluent streams from the respective reforming units for synthesis into F-T liquids needs to have specific molar ratios of $H_2$ to CO without regard to the $CO_2$ content of the this combined effluent steam. In particular, the molar ratio of $H_2$ to CO should be greater than about 1.9 and more preferably in the range of from about 2.0 to 2.8. Most preferably, the $H_2$ to CO molar ratio in the combined syngas blend will range from about 2.1 to 2.6.

Finally, the combined effluent stream from the respective reforming units used in the present process must have an absolute limit on the amount of $CO_2$ contained therein. On a water-free basis, the $CO_2$ content of the combined effluent stream should be less than about 5.5 mol %. More preferably, the $CO_2$ content of the combined effluent stream should range from about 2 mol % to 5 mol %, more preferably from about 2.5 mol % to 4.5 mol %, on a water free basis.

The absolute and relative amounts of $H_2$, CO and $CO_2$ in the combined syngas effluent stream from the two types of reforming units utilized herein can be controlled and altered by adjusting the operating conditions within one or both of the reforming units and/or by changing the relative amounts of gaseous hydrocarbon feedstreams fed to each type of reforming unit. It is also possible to alter the $S_N$ ratio and the absolute $CO_2$ content of the combined syngas blend by removing, and optionally recycling, some of the $CO_2$ from one or more of the syngas steams involved in the process. Several commercial technologies are available to recover and recycle $CO_2$ from the syngas effluent streams herein. In one embodiment, $CO_2$ can be recovered from the syngas effluent from the steam reforming unit, and such recovered $CO_2$ can be recycled to the steam reformer.

In one embodiment of the present invention, the combined syngas effluent stream produced as described hereinbefore can be use as a synthesis gas feedstock for the production of Fischer-Tropsch (F-T) liquids. The catalytic production of such F-T liquids (which are generally higher hydrocarbon materials) from synthesis gas, i.e. carbon monoxide and hydrogen, is represented by the equation hereinbefore set forth.

The hydrocarbon products and derivatives thereof of a typical Fischer-Tropsch process includes a wide variety of chemical components including oxygenates, olefins, esters, and paraffins, many of which can be gaseous or liquid at reaction conditions. These Fischer-Tropsch products have benefits over those obtained via traditional refining processes in that the materials are essentially free of sulfur, metals, nitrogen-containing compounds and aromatics.

The Fischer-Tropsch process depends on the use of specialized catalysts. The original catalysts for Fischer-Tropsch synthesis were typically Group VIII metals, particularly cobalt and iron, which have been adopted in the process throughout the years to produce higher hydrocarbons. As the technology has developed, these catalysts became more refined and were augmented by other metals that function to promote their activity as catalysts. Such promoter metals include the Group VIII metals, such as platinum, palladium, ruthenium, and iridium, other transition metals such as rhenium and hafnium as well as alkali metals. Preferred Fischer-Tropsch catalysts are supported on an inorganic refractory oxide selected from Groups III, IV, V, VI, and VIII of the Periodic Chart. Preferred supports include silica, alumina, silica-alumina, the Group IVB oxides, most preferably titania, such as those disclosed, e.g. in U.S. Pat. No. 5,128,377, incorporated herein by reference. The choice of a particular metal or alloy for fabricating a catalyst to be utilized in Fischer-Tropsch synthesis will depend in large measure on the desired product or products.

In another embodiment of the present invention, the combined syngas effluent stream produced as described hereinbefore can be used as a synthesis gas feedstock for the catalytic production of oxygenates such as methanol, dimethyl ether, combinations of methanol and dimethyl ether and a wide variety of related oxygenates along with various by-products.

The catalyst used in the oxygenate synthesis process generally includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In a preferred embodiment, the catalyst used in the oxygenate synthesis process is a copper based catalyst, which also includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

In embodiments in which copper oxide and zinc oxide are both present in the oxygenate synthesis catalyst, the ratio of copper oxide to zinc oxide can vary over a wide range. Preferably in such embodiments, the oxygenate synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The oxygenate synthesis catalyst can be made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the syngas blend formed in accordance with the present invention is cooled prior to being sent to the oxygenate synthesis reactor. Preferably, the syngas is cooled so as to condense at least a portion of the water vapor formed during the syngas process.

The oxygenate synthesis process implemented in the present invention can be any conventional methanol or other oxygenate synthesis process. Examples of such processes include batch processes and continuous processes. Continuous processes are preferred. Tubular bed processes and fluidized bed processes are particularly preferred types of continuous processes.

The oxygenate synthesis process is effective over a wide range of temperatures. In one embodiment, the syngas blend is contacted with the oxygenate synthesis catalyst at a temperature in the range of from about 302° F. (150° C.) to about 842° F. (450° C.), preferably in a range of from about 347° F. (175° C.) to about 662° F. (350° C.), more preferably in a range of from about 392° F. (200° C.) to about 572° F. (300° C.).

The oxygenate synthesis process is also operable over a wide range of pressures. In one embodiment, the syngas blend contacted with the oxygenate synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities for oxygenate synthesis vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

The oxygenate synthesis procedure produces a crude methanol product containing a variety of materials as by-products. According to the oxygenate synthesis aspects of this invention, it is desirable to operate the process so as to maximize not only the amount of methanol formed, but also other alcohols, ethers, aldehydes and other oxygenates which are particularly desirable in the conversion of oxygenates to olefins. In is particularly appropriate to maximize the amount of methanol formed in the oxygenate synthesis, and remove hydrocarbons less desirable in the conversion of oxygenates to olefins from the crude methanol product stream formed in the oxygenate synthesis reactor.

In accordance with preferred embodiments of this invention, the crude methanol product mixture formed in the oxygenate synthesis unit can be further processed after reaction to obtain a desirable refined methanol-containing composition suitable for further processing, particularly in an oxygenate-to-olefins (OTO) operation. Refining of the crude methanol product can be accomplished by any conventional means. Examples of such means include distillation, selective condensation, and selective adsorption. Process conditions, e.g., temperatures and pressures, can vary according to the particular methanol composition desired. Various means for refining the crude methanol products produced via oxygenate synthesis operations are disclosed in U.S. Patent Application Publication No. 2005/0107482, incorporated herein by reference.

It is particularly desirable to minimize the amount of water and light boiling point components in the methanol-containing composition, but without substantially reducing the amount of methanol and desirable ethers, aldehydes and/or other desirable alcohols also present. Low-water methanol compositions are preferred oxygenate material which can be produced from the syngas blends herein. For purposes of this invention, low-water methanol compositions are those containing less than 10 mol % of water, preferably less than 5 mol % of water.

As indicated, one embodiment of the present invention provides for combining a methanol synthesis system with an oxygenates to olefins (OTO) reaction process. In an OTO process, typically an oxygenated feedstock, most preferably a methanol-containing feedstock, is converted in the presence of a molecular sieve catalyst composition into one or more olefins, preferably and predominantly, ethylene and/or propylene, referred to herein as light olefins.

Typically, molecular sieve catalysts have been used to convert oxygenate compounds to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

In a preferred embodiment of an integrated process of this invention, the feedstock contains one or more oxygenates in addition to methanol or, more specifically, one or more organic compounds containing at least one oxygen atom. In the most preferred embodiment of the process of invention, the oxygenates in the feedstock (in addition to methanol) comprise one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates, in addition to methanol include ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises methanol, and one or more of DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

The process for converting a feedstock containing one or more oxygenates, in the presence of a molecular sieve catalyst composition, is carried out in a reaction process in a reactor, where the process is a fixed bed process, a fluidized bed process (includes a turbulent bed process), preferably a continuous fluidized bed process, and most preferably a continuous high velocity fluidized bed process.

The conversion temperature employed in the OTO conversion process, within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the OTO conversion process, within the reactor system, varies over a wide range including autogenous pressure. The conversion pressure is based on the partial pressure of the feedstock exclusive of any diluent therein. Typically the conversion pressure employed in the process is in the range of from about 0.1 kpaa to about 5 MPaa, preferably from about 5 kpaa to about 1 MPaa, and most preferably from about 20 kpaa to about 500 kpaa.

The weight hourly space velocity (WHSV), particularly in an OTO process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is typically maintained at a level sufficient to keep the catalyst composition in a fluidized state within a reactor.

Typically, the WHSV ranges for OTO processes from about 1 hr-1 to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol, DME, or both, is in the range of from about 20 hr$^{-1}$ to about 300 hr$^{-1}$.

Figure 1:
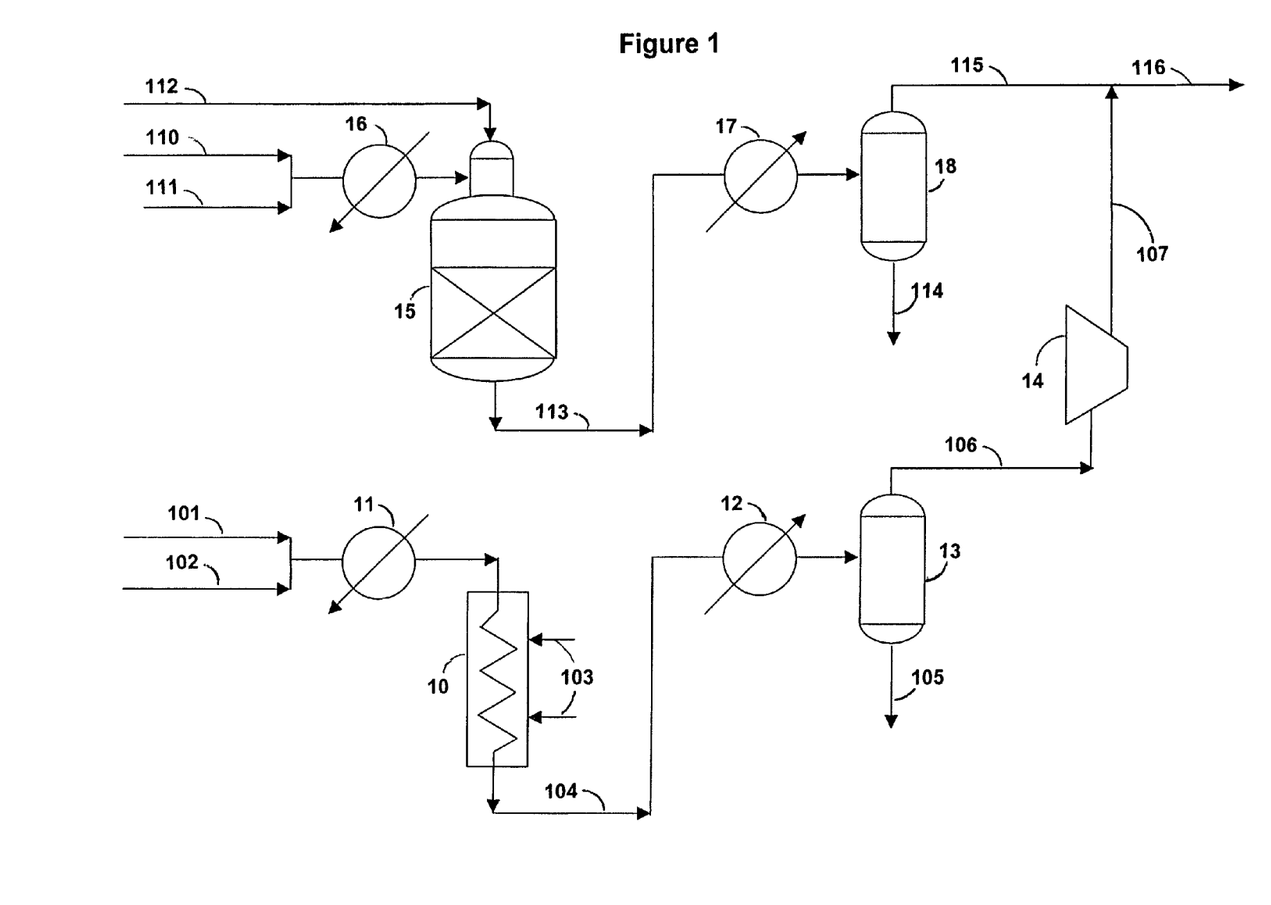
FIG. 1 is a flow diagram of a process for producing a synthesis gas blend by combining syngas effluent from both a steam reforming unit and an autothermal reforming unit.
Figure 2:
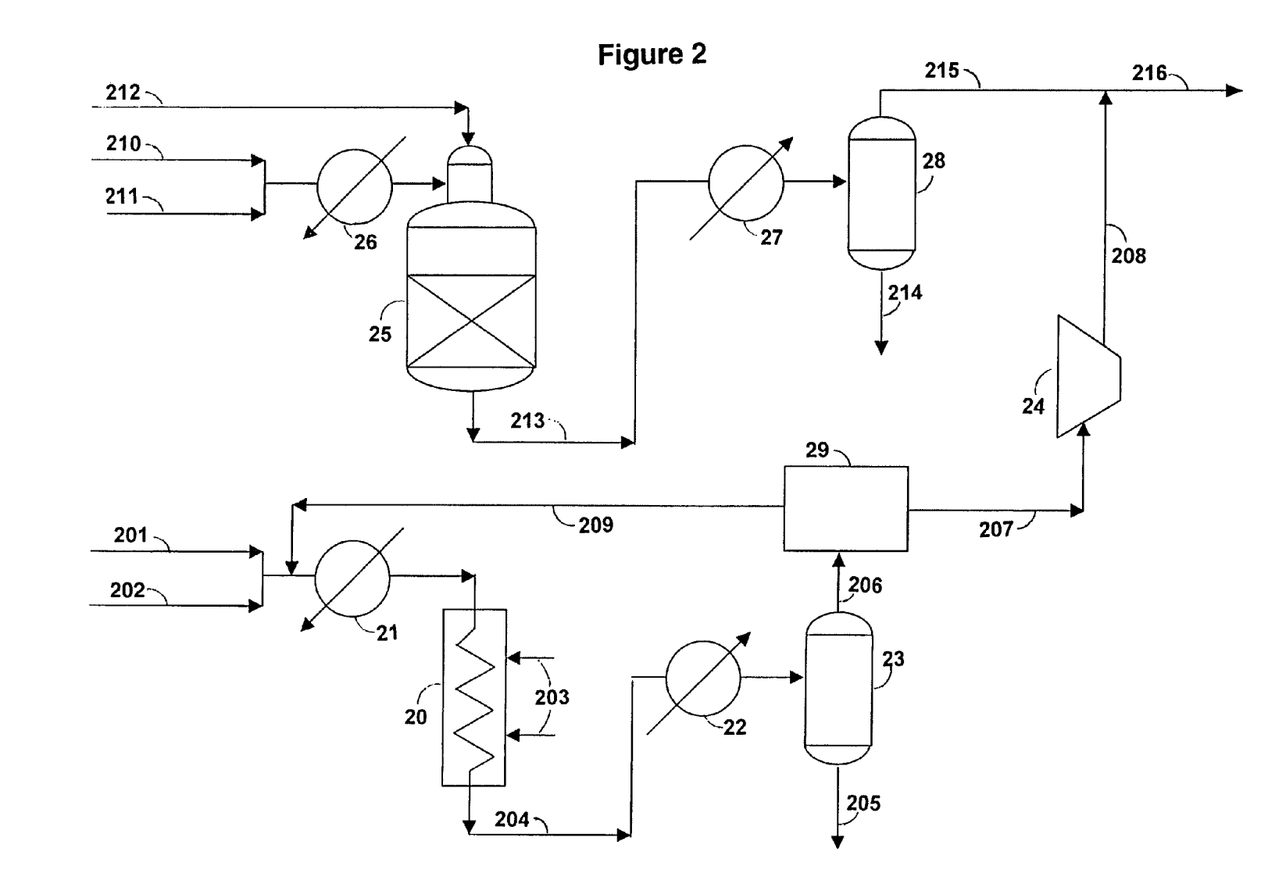
FIG. 2 is a flow diagram of process for producing a synthesis gas blend by combining syngas effluent from both a steam reforming unit and an autothermal reforming unit and with $CO_2$ recovered from the steam reforming unit and recycled thereto.
Figure 3:
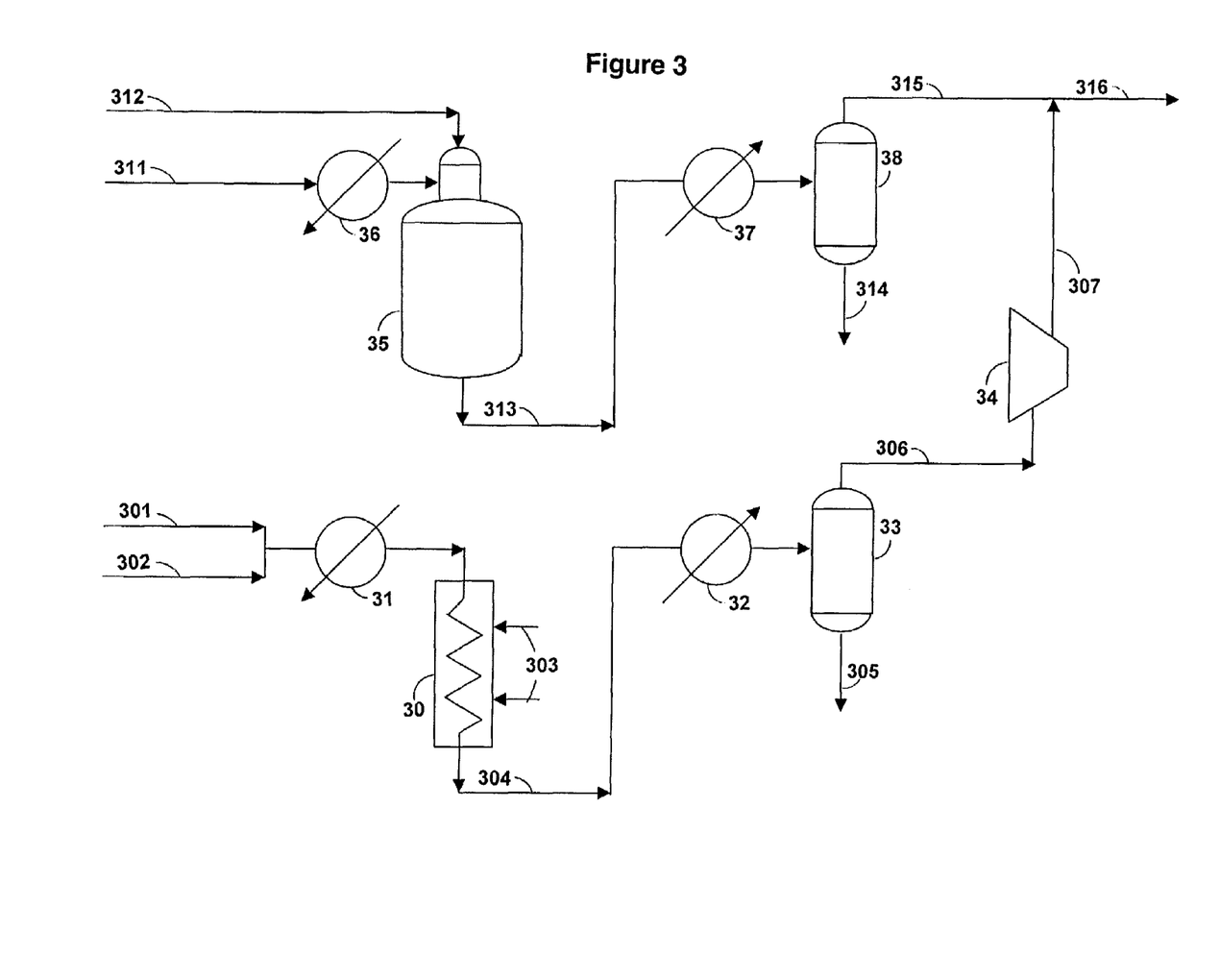
FIG. 3 is a flow diagram of a process for producing a synthesis gas blend by combining syngas effluent from both a steam reforming unit and an partial oxidation reforming unit.

The reforming operations of the present process are illustrated by the three figures set forth in the drawings. FIG. 1 shows one embodiment of the synthesis gas preparation process of the present invention. In this embodiment, sygas is prepared in both a steam reforming operation and in an autothermal reforming operation. Details of this process are those set forth in Example 1 hereinafter.

In the steam reforming portion of this FIG. 1 process, steam is fed via line 101 and natural gas is fed via line 102 to a steam reforming unit 10 after the combined steam and natural gas feeds are heated in heater 11. The endothermic reaction in the steam reformer 10 is promoted by means of heat supplied to the steam reforming unit 10 via lines 103. The syngas effluent from the steam reformer 10 is fed via line 104 through a cooler 12 to a separator 13. In the separator 13 water is condensed from the syngas and is taken from the separator 13 via line 105. Dewatered syngas is drawn from the separator 13 as overhead via line 106. This syngas stream 106 is then compressed in compressor 14 from which it is taken via line 107 for combination with another syngas blend prepared via the autothermal reforming portion of this process.

In the autothermal reforming portion of this FIG. 1 process, steam is fed via line 110 and natural gas is fed via line 111 to an autothermal reforming unit 15 after the combined steam and natural gas feeds are heated in heater 16. Oxygen is also fed via line 112 to the autothermal reforming unit 15. The reactions in the autothermal reformer 15 are both endothermic and exothermic with the endothermic steam reforming reaction using heat supplied by the exothermic oxygen reforming reaction. The syngas effluent from the autothermal reformer 15 is fed via line 113 through a cooler 17 to a separator 18. In the separator 18 water is condensed from the syngas and is taken from the separator 18 via line 114. Dewatered syngas is drawn from the separator 18 as overhead via line 115. This syngas stream 115 is then combined with syngas from line 107 coming from the steam reforming operation.

The combined syngas stream is then withdrawn from the FIG. 1 process via line 116. Syngas from line 116 can then be used for either synthesis of Fischer-Tropsch liquids or for preparation of oxygenates such as the crude methanol product produced via methanol synthesis from syngas.

FIG. 2 shows another embodiment of the synthesis gas preparation process of the present invention. In this embodiment, syngas is prepared in both a steam reforming operation and in an autothermal reforming operation with the steam reforming operation involving removal and recycle of $CO_2$. Details of this process are those set forth in Example 2 hereinafter.

In the steam reforming portion of this FIG. 2 process, steam is fed via line 201 and natural gas is fed via line 202 to a steam reforming unit 20 after the combined steam and nature gas feeds are heated in heater 21. The endothermic reaction in the steam reformer 20 is promoted by means of heat supplied to the steam reforming unit 20 via lines 203. The syngas effluent from the steam reformer 20 is fed via line 204 through a cooler 22 to a separator 23. In the separator 23 water is condensed from the syngas and is taken from the separator 23 via line 205. Dewatered syngas is drawn from the separator 23 as overhead via line 206. This syngas stream 206 is then fed to a $CO_2$ removal unit 29. $CO_2$ separated from the syngas stream 206 in the $CO_2$ separator 29 is fed from the $CO_2$ separator 29 via line 209 as recycle for addition to the combined steam and natural gas feeds prior to heater 21. Syngas with lowered $CO_2$ content is drawn from the $CO_2$ removal unit 29 via line 207. Syngas from this line 207 is compressed in compressor 24 from which it is taken via line 208 for combination with another syngas blend prepared via the autothermal reforming portion of this FIG. 2 process.

In the autothermal reforming portion of this FIG. 2 process, steam is fed via line 210 and natural gas is fed via line 211 to an autothermal reforming unit 25 after the combined steam and natural gas feeds are heated in heater 26. Oxygen is also fed via line 212 to the autothermal reforming unit 25. The reactions in the autothermal reformer 25 are both endothermic and exothermic with the endothermic steam reforming reaction using heat supplied by the exothermic oxygen reforming reaction. The syngas effluent from the autothermal reformer 25 is fed via line 213 through a cooler 27 to a separator 28. In the separator 28 water is condensed from the syngas and is taken from the separator 28 via line 214. Dewatered syngas is drawn from the separator 28 as overhead via line 215. The syngas stream 215 is then combined with syngas from line 208 coming from the steam reforming operation.

The combined syngas stream is then withdrawn from the FIG. 2 process via line 216. Syngas from line 216 can then be used for either synthesis of Fischer-Tropsch liquids or for preparation of oxygenates such as the crude methanol product produced via methanol synthesis from syngas.

FIG. 3 shows yet another embodiment of the synthesis gas preparation process of the present invention. In this embodiment, syngas is prepared in both a steam reforming operation and in a partial oxidation (POX) reforming operation. Details of this process are those set forth in Example 3 hereinafter.

In the steam reforming portion of this FIG. 3 process, steam is fed via line 301 and natural gas is fed via line 302 to a steam reforming unit 30 after the combined steam and nature gas feeds are heated in heater 31. The endothermic reaction in the steam reformer 30 is promoted by means of heat supplied to the steam reforming unit 30 via lines 303. The syngas effluent from the steam reformer 30 is fed via line 304 through a cooler 32 to a separator 33. In the separator 33 water is condensed from the syngas and is taken from the separator 33 via line 305. Dewatered syngas is drawn from the separator 33 as overhead via line 306. This syngas stream 306 is then pressurized in compressor 34 from which it is taken via line 307 for combination with another syngas blend prepared via the partial oxidation reforming portion of this FIG. 3 process.

In the partial oxidation (POX) reforming portion of this FIG. 3 process, no steam is fed to the POX reforming unit 35. However, natural gas is fed via line 311 to the partial oxidation (POX) reforming unit 35 after the natural gas feed is heated in heater 36. Oxygen is also fed via line 312 to the partial oxidation (POX) reforming unit 35. The reaction in the partial oxidation reformer 35 is exothermic and proceeds without a catalyst. Accordingly, very high temperatures and pressures can be used in the POX reforming unit 35. The syngas effluent from the partial oxidation reformer 35 is fed via line 313 through a cooler 37 to a separator 38. In the separator 38 water is condensed from the syngas and is taken from the separator 38 via line 314. Dewatered syngas is drawn from the separator 38 as overhead via line 315. This syngas stream 315 is then combined with syngas from line 307 coming from the steam reforming operation.

The combined syngas stream is then withdrawn from the FIG. 3 process via line 316. Syngas from line 316 can then be used for either synthesis of Fischer-Tropsch liquids or for preparation of oxygenates such as the crude methanol product produced via methanol synthesis from syngas.

EXAMPLES

In the following examples, the improved syngas preparation procedure of the present invention is shown in comparison with several conventional natural gas reforming techniques which produce syngas mixtures that are less optimal for subsequent conversion to oxygenates or Fischer-Tropsch liquids. The initial Examples A, B, C and D hereinafter illustrate conventional reforming processes. Examples 1, 2 and 3 illustrate embodiments of the syngas preparation process of the present invention.

Examples A, B, C and D show the reforming conditions and syngas compositions produced from four commercial reformers. The syngas compositions are calculated based on thermodynamic equilibrium of all possible components at the conditions at the exit of the reformer. It can be seen that each of these examples produces a non-optimum composition for either methanol synthesis, F-T synthesis, or both.

In each example, the hydrocarbon feedstock to the reformer is a natural gas with 89.7 mol % methane, 5.5 mol % ethane, and 4.8 mol % nitrogen (molar basis). Table 1 contains a summary of the reaction conditions the results of the reaction equilibrium calculations for Examples A, B, C and D.

Example A

Autothermal Reforming

Autothermal reforming (ATR) as noted hereinbefore is the addition of air or oxygen to the hydrocarbon feedstock to generate sufficient heat to drive the endothermic reforming reactions over a bed of catalyst. There is no external heat provided to any reaction zone. An advantage of ATR is its ability to run at high temperatures, low steam:carbon ratios, and high pressures. In this example, an ATR reactor is run on oxygen with an $O_2$:C ratio of 0.53, a steam:carbon ratio of 0.6, and a pressure of 45 bar. As shown in Table 1, the resultant syngas has a $S_N$ value of 1.84 and an $H_2$:CO ratio of 2.25. This syngas composition has a slight surplus of hydrogen for F-T synthesis, but has inadequate hydrogen for methanol synthesis. The $CO_2$ content is 4.1%, a fairly low value which is desirable for both F-T and methanol synthesis.

It would be desirable to have a means to adjust the stoichiometry of the syngas from an ATR to make it more desirable for methanol synthesis, by the addition of hydrogen.

Example B

Steam Reforming

Steam Reforming (SR) as noted hereinbefore is the reforming of a hydrocarbon by reaction with steam where all the heat is supplied external to the catalyst bed(s), and no oxygen is contained in the feed. Commercial technologies utilize nickel catalysts, and a relatively large ratio of steam:carbon is required to prevent coking of the catalyst. Due to the need to transfer heat to the catalyst bed, metal tubes must be utilized and heat is transferred across the tubes, typically with fired heat. The strength of the tube metal typically limits the reformer gas exit temperature to about 875° C. In order to achieve high conversion at this temperature, the pressure must be kept relatively low; typically below 25 bar. In Example B as shown in Table 1, a reformer with a steam:carbon ratio of 3.5 operates at 25 bar and with an exit temperature of 875° C. achieves a $S_N$ value of 2.94 and an $H_2$:CO ratio of 5.53. This syngas composition contains excessive hydrogen for either methanol or F-T synthesis. In addition, the $CO_2$ content of 8.7% is also excessive for either methanol or F-T synthesis.

It would be desirable to have a means to adjust the stoichiometry of the syngas from a SR to provide more carbon oxides.

Example C

Combined Reforming

Combined Reforming (CR) is defined here as the combination of SR and ATR. Steam is mixed with the hydrocarbon feed and at least partially converted to syngas in a SR with external heat transfer. This external heat transfer can either be provided by fired heat, or by heat exchange with the ATR effluent. An ATR reforms at least part of the hydrocarbon feedstock, either as a parallel reaction, in series with the SR, or a combination of both series and parallel operation. Both the ATR and the SR operate at approximately the same pressures. In this Example C, an SR in series with an ATR is operated at 45 bar, with a steam:carbon ratio of 2.0, and an $O_2$:C ratio of 0.42. As shown in Table 1, the resulting syngas has a $S_N$ value of 2.07 and an $H_2$:CO ratio of 3.27. This syngas composition has excessive hydrogen for F-T synthesis, but is ideal for methanol synthesis. The $CO_2$ content is 8.1%, which is high for methanol synthesis technologies where minimization of water production is desired.

Combined reforming allows the $S_N$ value to be adjusted to match the desired level for methanol synthesis. However, the $CO_2$ content is higher than is desirable for methanol synthesis technologies where the production of water must be minimized. The high $CO_2$ content is due to the fact that the SR portion of the reaction requires a relatively high steam:carbon ratio, which results in a higher $CO_2$ content due to the water gas shift Reaction No. (3), set forth above.

Example D

Partial Oxidation Reforming

Partial Oxidation (POX) reforming, as noted hereinbefore, involves the reaction of a hydrocarbon feedstock with an oxygen-containing gas without any catalyst. Due to the absence of catalyst, a POX reactor can operate at very high temperatures and with little or no steam addition. The high temperature capability allows the pressure to be higher than an ATR. In Example D, a POX reformer is operated with an $O_2$:C ratio of 0.63, a steam:carbon ratio of 0.0, and a pressure of 80 bar. The resultant syngas composition has a $S_N$ value of 1.67 and an $H_2$:CO ratio of 1.78. This syngas composition is hydrogen deficient for either methanol or F-T synthesis. The $CO_2$ content has a very low value of 1.4%, which is desirable for F-T synthesis but below the optimum value for methanol synthesis.

It would be desirable to increase the hydrogen content of syngas from a POX reformer.

TABLE 1

Reformer Conditions and Syngas Compositions for Examples A-D

| | Example Number | | | |
|---|---|---|---|---|
| | Example A | Example B | Example C | Example D |
| | Method | | | |
| | ATR Only | Steam Reforming | Combined Reforming | POX |
| Reformer Pressure, bar | 45 | 25 | 45 | 80 |
| Final Reformer Exit Temperature, ° C. | 1096 | 875 | 1020 | 1351 |
| O2:C ratio | 0.53 | 0.0 | 0.42 | 0.63 |
| H2O:C ratio | 0.6 | 3.5 | 2.0 | 0.0 |
| Product Syngas Composition, mol % | | | | |
| Methane | 1.4% | 3.3% | 1.1% | 0.6% |
| H2O | 0.3% | 0.5% | 0.3% | 0.1% |
| CO | 28.4% | 13.2% | 20.8% | 34.3% |
| CO2 | 4.1% | 8.7% | 8.1% | 1.4% |
| H2 | 63.9% | 73.1% | 68.1% | 61.3% |
| N2 | 2.0% | 1.2% | 1.7% | 2.2% |
| Stoich Number (H2 − CO2)/(CO + CO2) | 1.84 | 2.94 | 2.07 | 1.67 |
| H2/CO Ratio | 2.25 | 5.53 | 3.27 | 1.78 |

The following Examples 1-3 illustrate three embodiments of the present invention. The apparatus arrangements for each of these three examples are the ones shown in FIGS. 1-3, respectively. These examples utilize the same natural gas composition as in Examples A-D.

Table 2 hereinafter lists the reformer conditions and syngas compositions for these Examples 1-3. In Table 2, the term "OBR" is used to designate an "Oxygen-Blown Reformer", of which autothermal reforming and partial oxidation reforming are both sub-categories.

Example 1

ATR+SR

In this Example 1, the natural gas feedstock is split such that 76.2% of the feed is reformed in an ATR and the remainder is reformed in a SR. The ATR is operated at 45 bar, with an $O_2$:C ratio of 0.53, a steam:carbon ratio of 0.6, and a reformer exit equilibrium temperature of 1096° C. The SR is operated at 25 bar, with no oxygen addition, with a steam:carbon ratio of 3.5, and a reformer exit equilibrium temperature of 875° C. The syngas from the SR is compressed and blended with the ATR syngas. As shown in Table 2, the resulting $S_N$ is 2.08 and the $H_2$:CO ratio is 2.79. The $CO_2$ content of the syngas blend is 5.5%.

For methanol synthesis, the $S_N$ value is optimum and is an improvement over Examples A, B, and D. The $CO_2$ content of 5.5% is lower than that of Examples B or C. The total oxygen demand per mole of carbon is 0.40, which is substantially lower than Examples A or D and slightly lower than Example C. The total steam:carbon ratio is 1.29, which is lower than either Examples B or C. These results show that the embodiment of Example 1 represents an improvement in both syngas composition and utility demands over any of the base cases for the synthesis of methanol.

For F-T synthesis, the $H_2$:CO ratio is improved over Examples B, C, and D. The $CO_2$ content is lower than either Examples B or C.

Example 2

ATR+SR with $CO_2$ Recovery and Recycle

In this Example 2, the natural gas feedstock is split and fed to ATR and SR reformers just as in Example 1. A $CO_2$ recovery unit is added to the syngas produced from the SR, and the recovered $CO_2$ is recycled back to the SR feed. There are several commercial technologies available to recover and recycle $CO_2$, which are known to those skilled in the art. As shown in Table 2, an 80% recovery of $CO_2$ from the SR syngas reduces the $CO_2$ content in syngas blend from 5.5% to 3.8%. This embodiment has all of the advantages for methanol synthesis mentioned in Example 1, plus it has a lower syngas $CO_2$ content than Example A as well. This syngas composition is highly desirable for methanol synthesis, since it achieves the optimum $S_N$ value and has a low $CO_2$ content that minimizes water production in the methanol synthesis section.

Example 3

POX+SR

In this Example 3, the natural gas feedstock is split such that 64.5% of the feed is reformed in a POX reformer and the remainder is reformed in a SR. The POX reformer is operated at 80 bar, with an $O_2$:C ratio of 0.63, a steam:carbon ratio of 0.0, and a reformer exit equilibrium temperature of 1351° C. The SR is operated at 25 bar, with no oxygen addition, with a steam:carbon ratio of 3.5, and a reformer exit equilibrium temperature of 875° C. The syngas from the SR is compressed and blended with the POX syngas. As shown in Table 2, the resulting $S_N$ is 2.09 and the $H_2$:CO ratio is 2.66. The $CO_2$ content of the syngas blend is 4.7%.

For methanol synthesis, the $S_N$ value is optimum and is an improvement over Examples A, B, and D. The $CO_2$ content of 4.7% is lower than that of Examples B or C. The total oxygen demand per mole of carbon is 0.40, which is substantially lower than Examples A or D and slightly lower than Example C. The total steam:carbon ratio is 1.24, which is lower than either Examples B or C. These results show that the embodiment of Example 3 represents an improvement in both syngas composition and utility demands over any of the Examples A-D for the synthesis of methanol.

For F-T synthesis, the $H_2$:CO ratio is improved over Examples B, C, and D. The $CO_2$ content is lower than either Examples B or C.

TABLE 2

Reformer Conditions and Syngas Compositions for Examples 1-3

| | Example Number | | |
|---|---|---|---|
| | Example 1 | Example 2 | Example 3 |
| | | Method | |
| | ATR + SR | ATR + SR with CO2 recovery & recycle | POX + SR |
| Natural gas feed rate, kgmol/h | 26783 | 26783 | 26783 |
| OBR Pressure, bar | 45 | 45 | 80 |
| SR Pressure, bar | 25 | 25 | 25 |
| AOBR Exit Temperature, ° C. | 1096 | 1096 | 1351 |
| SR Exit Temperature, ° C. | 875 | 875 | 875 |
| Fraction Feed to OBR | 0.762 | 0.762 | 0.645 |
| O2:C ratio to OBR | 0.53 | 0.53 | 0.63 |
| O2:C ratio to SR | 0.0 | 0.0 | 0.0 |
| Overall O2:C Ratio | 0.40 | 0.40 | 0.40 |
| H2O:C ratio to OBR | 0.6 | 0.6 | 0 |
| H2O:C ratio to SR | 3.5 | 3.5 | 3.5 |
| Overall H2O:C ratio | 1.29 | 1.29 | 1.24 |
| Syngas Composition from OBR, mol % | | | |
| Methane | 1.4% | 1.4% | 0.6% |
| H2O | 0.3% | 0.3% | 0.1% |
| CO | 28.4% | 28.4% | 34.3% |
| CO2 | 4.1% | 4.1% | 1.4% |
| H2 | 63.9% | 63.9% | 61.3% |
| N2 | 2.0% | 2.0% | 2.2% |
| Stoich Number (H2 − CO2)/(CO + CO2) | 1.84 | 1.84 | 1.67 |
| H2/CO Ratio | 2.25 | 2.25 | 1.78 |
| Syngas Composition from SR, mol % | | | |
| Methane | 3.3% | 3.2% | 3.3% |
| H2O | 0.5% | 0.5% | 0.5% |
| CO | 13.2% | 20.2% | 13.2% |
| CO2 | 8.7% | 3.1% | 8.7% |
| H2 | 73.1% | 71.8% | 73.1% |
| N2 | 1.2% | 1.3% | 1.2% |
| Stoich Number (H2 − CO2)/(CO + CO2) | 2.94 | 2.95 | 2.94 |
| H2/CO Ratio | 5.53 | 3.56 | 5.53 |
| Combined Syngas Composition, mol % | | | |
| Methane | 1.9% | 1.9% | 1.8% |
| H2O | 0.3% | 0.3% | 0.3% |
| CO | 23.9% | 26.1% | 25.0% |
| CO2 | 5.5% | 3.8% | 4.7% |
| H2 | 66.6% | 66.1% | 66.5% |
| N2 | 1.8% | 1.8% | 1.8% |
| Stoich Number (H2 − CO2)/(CO + CO2) | 2.08 | 2.09 | 2.09 |
| H2/CO Ratio | 2.79 | 2.54 | 2.66 |

We claim:

1. A process for the production of a synthesis gas blend which is suitable for conversion either to methanol and/or dimethyl ether or to Fischer-Tropsch liquids, which process comprises:
   a) passing a first gaseous hydrocarbon feedstream, along with steam, to a steam reforming unit operated at a pressure of less than 30 bar and with a steam to carbon molar ratio greater than 1.5, thereby providing as effluent from said steam reforming unit a first syngas effluent stream containing $H_2$ and carbon oxides;
   b) passing a second gaseous hydrocarbon feedstream, along with oxygen and optionally steam, to an oxygen-blown reforming unit operated at a pressure of greater than 35 bar and with an $O_2$:C molar ratio of from about 0.4 to 0.7 and a steam to carbon molar ratio of less than about 1.5, thereby providing as effluent from said oxygen-blown reforming unit a second syngas effluent stream containing $H_2$ and carbon oxides;
   c) compressing said first syngas effluent stream to a pressure substantially equal to that of said second syngas effluent stream; and thereafter
   d) combining said first and second syngas effluent streams in a ratio suitable to provide a syngas blend effluent having:
      i) a Stoichiometric Ratio $S_N$ ranging from about 2.0 to 2.2;
      ii) an $H_2$/CO molar ratio greater than about 1.9; and
      iii) a $CO_2$ content of about 5.5 mol % or less.

2. A process according to claim 1 wherein the first and second gaseous feedstreams each contain at least 50 mol % of methane.

3. A process according to claim 2 wherein said first and second gaseous hydrocarbon feedstreams have substantially the same methane content.

4. A process according to claim 3 wherein said first and second gaseous hydrocarbon feedstreams are formed by dividing a natural gas feedstock.

5. A process according to claim 3 wherein the ratio of moles/hr of methane in said first gaseous hydrocarbon feedstream to moles/hr of methane in said second gaseous hydrocarbon feedstream ranges from about 1:1 to 1:4.

6. A process according to claim 4 wherein the total natural gas feed rate to the process ranges from about 750 kgmol/hr to 45,000 kgmol/hr.

7. A process according to claim 1 wherein the steam reforming unit is operated at a pressure ranging from about 10 to 28 bar and an exit temperature of from about 750° C. to 950° C., using a steam to carbon molar ratio ranging from about 1.8:1 to 4:1.

8. A process according to claim 7 wherein the steam reforming unit utilizes at least one catalyst comprising an active metal or metal oxide of Group 6 or Groups 8-10 of the Periodic Table of the Elements.

9. A process according to claim 8 wherein the oxygen-blown reforming unit is an autothermal reforming unit operated at a pressure ranging from about 37 to 45 bar and an exit temperature of from about 900° C. to 1150° C., using an $O_2$:C molar ratio ranging from about 0.5:1 to 0.65:1 and a steam to carbon molar ratio ranging from about 0.4:1 to 1:1.

10. A process according to claim 9 wherein the autothermal reforming unit utilizes a catalyst comprising at least one transition element selected from the group consisting of Ni, Co, Pd, Ru, Rh, Ir, Pt, Os, Fe and combinations thereof.

11. A process according to claim 8 wherein the oxygen-blown reforming unit is a partial oxidation reforming unit operated at a pressure ranging from about 50 to 100 bar and a exit temperature of from about 1100° C. to 1500° C., using an $O_2$:C molar ratio ranging from about 0.5:1 to 0.7:1.

12. A process according to claim 1 wherein the compressed first syngas effluent stream and the second syngas effluent stream are at a pressure of from about 35 to 100 bar.

13. A process according to claim 6 wherein the syngas blend effluent has:
a) a Stoichiometric Number $S_N$ which ranges from about 2.05 to 2.1;
b) an $H_2$/CO molar ratio of from about 2.0 to 2.8; and
c) a $CO_2$ content of from about 2 mol % to 5 mol %.

14. A process according to claim 13 wherein $CO_2$ is removed from one or more of the syngas effluent streams so as to reduce the $CO_2$ content in said syngas blend effluent to less than 4 mol %.

15. A process according to claim 14 wherein $CO_2$ is removed from the syngas effluent from the steam reforming unit and at least part of the $CO_2$ removed from said syngas effluent is recycled to the steam reforming unit.

16. A process for the production of Fischer-Tropsch liquids, which process comprises preparing a syngas blend according to the process recited in claim 1, and then contacting said syngas blend with an iron and/or cobalt-based Fischer-Tropsch catalyst under conditions suitable to convert at least part of said syngas blend to Fischer-Tropsch liquids.

17. A process for the production of an oxygenate product, which process comprises preparing a syngas blend according to the process recited in claim 1, and then contacting said syngas blend with one or more metal-containing conversion catalysts under conditions suitable to convert at least a part of said syngas blend to an oxygenate-containing product.

18. A process for the production of an oxygenate product comprising methanol, dimethyl ether or methanol/dimethyl ether blends, which process comprises preparing a syngas blend according to the process recited in claim 13, and then contacting said syngas blend with one or more metal-containing conversion catalysts under conditions suitable to convert at least part of said syngas blend to oxygenates comprising methanol and/or dimethyl ether and wherein the water content of said syngas blend is not reduced prior to its contact with said conversion catalyst.

19. A process for the production of light olefins from oxygenates, which process comprises preparing an oxygenate feedstock comprising methanol, dimethyl ether or methanol/dimethyl ether blends according to the process recited in claim 18, and then contacting said oxygenate feedstock with a molecular sieve catalyst under conditions suitable for converting at least a part of said oxygenate feedstock to light olefins.

* * * * *